United States Patent [19]

Abramson

[11] 3,951,062

[45] Apr. 20, 1976

[54] METHOD OF RECORDING MEDICAL AND SURGICAL PATIENT INFORMATION

[76] Inventor: Daniel J. Abramson, 2800 Greenvale St., Chevy Chase, Md. 20015

[22] Filed: Dec. 18, 1974

[21] Appl. No.: 533,997

[52] U.S. Cl. .............................. 101/426; 101/368; 101/372; 283/1 A; D64/10
[51] Int. Cl.² ........................................ B41M 3/00
[58] Field of Search ............. 101/32, 368, 369, 371, 101/372, 373, 426; 283/1 A; 35/7; D64/10

[56] References Cited
UNITED STATES PATENTS

| | | | |
|---|---|---|---|
| 628,766 | 7/1899 | Cooke | 101/373 |
| 1,014,260 | 1/1912 | Sanborn | 101/373 |
| 1,023,457 | 4/1912 | Cuntz | 283/1 A |
| 1,337,168 | 4/1920 | Uttmark | 283/1 A |
| 1,449,318 | 3/1923 | Fish | 283/1 A |
| 2,156,289 | 5/1939 | Hoy | 283/1 A |
| 2,223,849 | 12/1940 | Fogler et al. | 283/1 A |
| 2,918,731 | 12/1959 | Warhaftig et al. | 101/328 |
| 3,403,623 | 10/1968 | Blackwood | 101/368 |
| 3,477,715 | 11/1969 | Nekton | 101/368 X |
| 3,756,153 | 9/1973 | Cohen | 101/368 |
| 3,795,192 | 3/1974 | Robertson | 101/368 |

OTHER PUBLICATIONS
Catalog: Faymus, Pre–Inked Colorstamp, No. 169–ES, pp. 8, 9, Copyright 1967.

Dietzen Catalog, Copyright 1946, p. 34.

*Primary Examiner*—Edgar S. Burr
*Assistant Examiner*—Paul J. Hirsch
*Attorney, Agent, or Firm*—Alex Mazel

[57] ABSTRACT

Medical and surgical information, diagnostic findings, anatomical abnormalities and/or changes, and the like are rapidly and accurately recorded in a patient's chart by reproducting, duplicating or imprinting, as by stamping, an anatomical outline or graphic representation of the anatomical area involved, in the appropriate section of the patient's record, thereafter marking or noting on the reproduction or imprint,- or adjacent thereto, the findings, observations, diagnosis, size and location of lesions and the like. The imprint or reproduction can be made by means of a rubber stamp or similar ink transfer or reproducing device, which bears on one surface, the raised configuration of the anatomical outline or graphic representation thereof, which after inking can be applied to the proper section of the patient's chart. This method and device affords both time saving and extremely accurate patient record keeping for immediate and future reference.

7 Claims, 3 Drawing Figures

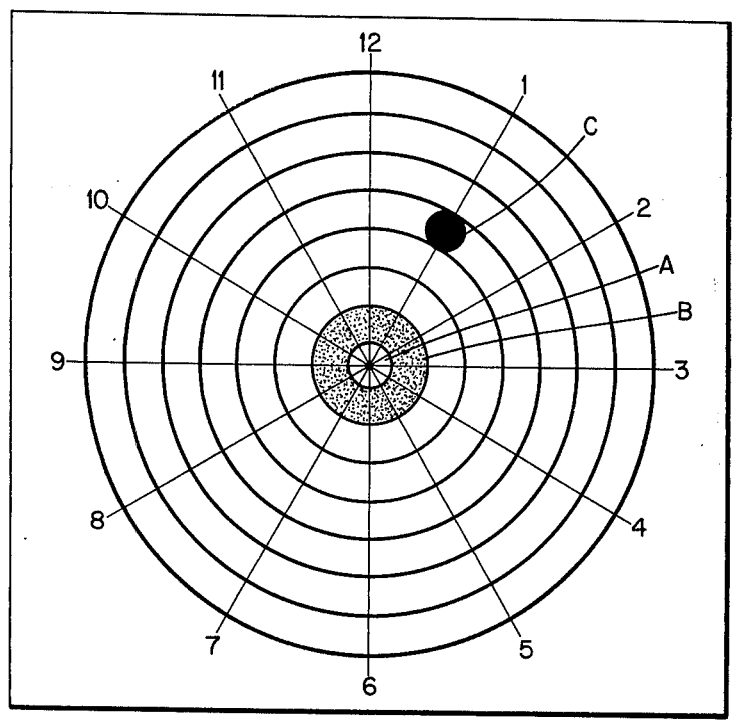
FIG. 1
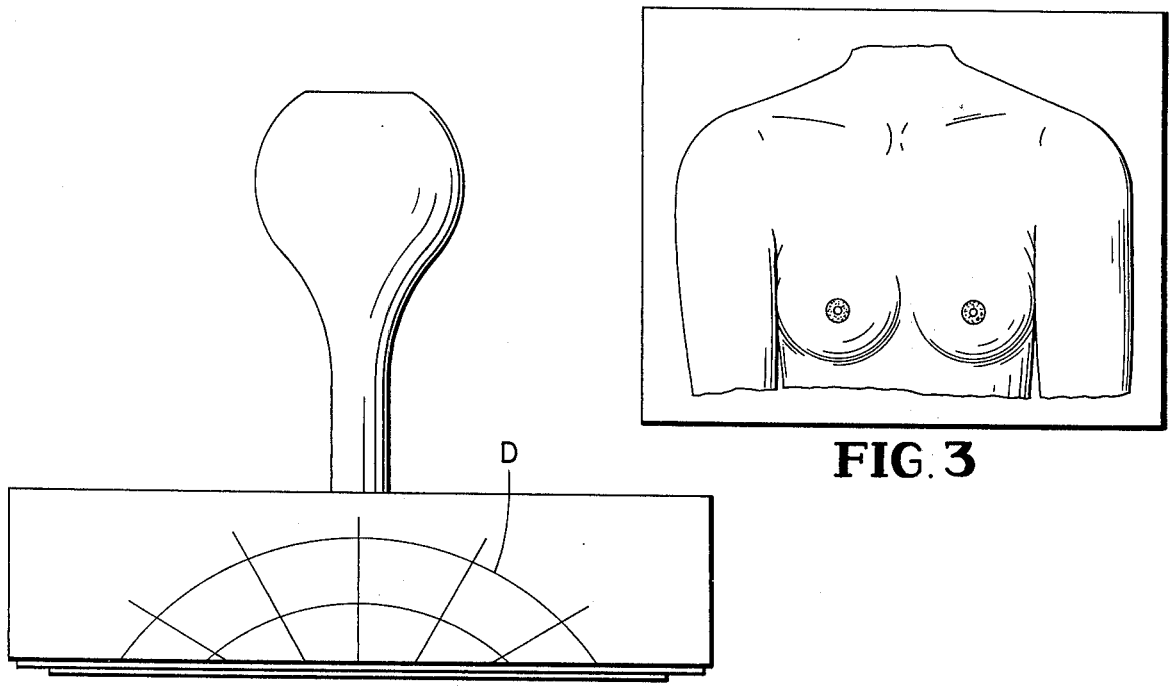
FIG. 2
FIG. 3

METHOD OF RECORDING MEDICAL AND SURGICAL PATIENT INFORMATION

BACKGROUND OF THE DISCLOSURE

Physicians and surgeons must keep medically and surgically accurate records of their patients. This can be a laborious and time consuming task, particularly where anatomical and surgical considerations are involved. For example, the high frequency of breast cancer in women and increasing public concern has led to many public campaigns and programs and frequent physician visits. It is imperative that frequent breast examinations of women be done and that all findings and abnormalities be accurately recorded, with the precise location thereof in the breasts, in relation to the nipple, for instance. Located masses must be recorded accurately as to location and size, and whether the mass is cystic, solid, thickening or neoplastic. Multiple cysts must be recorded as located on follow-up examination, all changes must be recorded, e.g. disappearance, increase in size or recurrence of cysts. Previously, physicians have had to resort to either lengthy descriptive medical and anatomical terminology to record their findings or to include a laboriously hand drawn rough drawing corresponding to the anatomical area, which is time consuming and not conducive to the necessary accuracy, as above indicated.

As another non-limiting example, ophthalmologists need to record their findings as to abnormalities of the eye to outline visual fields, peripheral visual delineation, blind spots and the like. The above considerations also apply.

As another example, urologists have to indicate size and location of genito-urinary abnormalities, e.g. size and location of a kidney stone and to plot its progress and/or growth in the system.

Similar problems of precise and convenient record keeping are to be found in diagnosis and treatment of diseases and abnormalities of the brain, heart, intestinal tract, lungs, the extremities and face, where the record must show the physician's findings, test (such as X-ray) results, type, size and location of abnormalities and changes therein.

It is acknowledged that large, individual anatomical charts exist as for classroom teaching and that smaller scale charts are to be found in textbooks. Also, dentists have available pre-printed standard diagrams of the teeth which are applicable to each and every human. However, in the practice of medicine and in surgery in particular, there are an infinitely greater number and variety of medical and surgical situations and conditions and locations thereof which must be described and noted in the patient's record both accurately and yet quickly, to conserve a busy physician's time. Thus, small scale anatomical diagrams or graphic representations thereof, which are instantaneously reproducible in the proper place in a patient's chart, considering the numerous possibilities would be of inestimable value in furthering accuracy in the necessary patient record keeping as well as enabling the physician to make the most efficient use of his time and meet the demands thereon. Prior to the present invention, no such method and means therefor, are known to have existed.

SUMMARY OF THE INVENTION

Briefly, the present invention provides a novel method and novel means therefor, for the quick and extremely accurate recording of medical, surgical and anatomical information in a patient's chart and or medical history. More specifically, the invention involves the use of a figure or diagram reproducing device, such as a rubber stamp or similar inked image transfer device, to make a fac-simile imprint or diagram of an anatomical area, or a graphic representation thereof, instantly, when and where required in a patient's record, and in the necessary scale. The physician can then note on the graphically clear anatomical diagram or representation, or adjacent thereto, his findings, observations, test results, location of abnormalities and the like, without the necessity for using lengthy and possibly imprecise terminology or hand drawing laboriously and roughly, an anatomical diagram. Not only does the invention provide immediate benefits in time saving and accuracy, — but lends itself to easy and accurate reference in follow-up examinations. The device employed would reproduce the exact same imprint or reproduction each time, without any variations.

BRIEF DESCRIPTION OF THE DRAWINGS

The above cited means for practicing the invention can best be illustrated by reference to specific examples and as shown in the accompanying drawings.

In FIG. 1, there is shown a plan view of the inking surface of a diagram representing a woman's breast. At the center, indicated by A is the nipple, B indicates the areola. As shown in FIG. 1, there is superimposed a series of concentric circles, the distance between the circles can represent one actual finger breadth as measured by the physician. The radial extensions from A represent the "hours" as on a timepiece. Thus, if a physician locates a cyst or mass in a woman's breast, two finger widths away from the nipple at the angle of one o'clock, he can so indicate the location on the diagram and further, make his mark in a way to indicate the size and type of the cyst or mass, for present and future reference. Thus, an irregular mark can indicate an irregular cyst and a solid mark can indicate a solid lesion. See C in FIG. 1. Other appropriate markings may be employed by the physician as necessary. Size of the markings can correspond to the relative size of the cyst or lesion. Different colors and shapes may be used. The shapes can correspond to the actual shapes, and different colors represent different types of lesions or masses.

FIG. 2 shows in side view, a rubber stamp, bearing on the side a guide D, spaced semi-circles and spaced angular lines, with a vertical line bisecting the semi-circles to enable the physician to align the reproduction or imprint of the anatomical diagram located on the lower face of the stamp, so as to occupy the desired space in the patient's chart. As indicated in FIG. 1, the diagram is of a size found suitable, but this size obviously can be one of choice depending on what area of the body is involved, how much detail is required and the like.

FIG. 3 indicates a type of stamp face contemplated in which the concentric circles and radial lines may be eliminated if desired, in favor of a more pictorial diagram, for other purposes of record keeping as dictated by the individual case. These figures are merely by way of illustrative example only and are in no way intended to be limiting as to the scope. Obviously, as indicated above, similar applications can be made with respect to other parts, areas and organs of the body as will occur to the practiner in the art within the scope of this

DESCRIPTION OF THE PREFERRED EMBODIMENTS

As indicated above, the high frequency of breast cancer in women has led to increased public concern and a great rise in the frequency of physician visits, with a greater demand on physician's time. Up until now, physicians have briefly as possible recorded their findings, in either lengthy medical or anatomical terminology or have tried to roughly chart their findings by hand drawing in the record. It is clearly imperative, that, in view of the necessity for frequent re-examinations as well, that the record be complete and as accurate as possible. Moreover, the demands on a physician's time are such, that ease and quickness of making the required record entries are also of great importance.

By use of such an anatomical diagram or graphic representation or reproduction device as shown in FIGS. 1, 2 and 3, or the like, the physician can reproduce, imprint or stamp in the patient's record said diagram and record his findings, e.g. of lesions as in the case of breast examinations as follows, by using appropriate markings and symbols:

1. Precise location in the breast (e.g. in relation to the nipple)
2. Type of the mass or lesion, e.g. cystic, solid, thickening, neoplastic.
3. Size and shape (irregular, etc.). Since the space between any two circles is one fingerbreadth, for example, the appropriate marking in area, will indicate the size of the mass. Otherwise, on FIG. 3, the size and contour can be indicated with respect to the whole breast or chest area.
4. Alongside the diagram, the physician can make other notes as to size, dimpling and retraction of the mass where such is indicated. A number of different marks are possible as needed, for shape, type of lesion, solid markings, or colors, if desired.
5. Follow-up examinations become more valuable and precise as a result of the invention. All changes are recorded, — disappearance, increase in size and recurrence of cysts. The invention is particularly valuable in recording multiple cysts and recurrences.
6. The inked reproduction device of the invention facilitates accurate recording of the findings and tests for the record, it removes the necessity for rough and inaccurate drawings. Masses are accurately placed and recorded for easy recall and changes are immediately evident or subsequent examination. Changes that occur with menstrual periods can easily and quickly be recorded. Reference is made to the "description of the drawings" above and are included herewith by way of illustration of this preferred embodiment.

A similar method and device can be used in charting findings in other parts of the body. As another non-limiting example, an ophthalmologist can indicate on a suitable reproducible chart stamped in the patient's record, location of abnormalities in the eye e.g. growths, — he can outline visual fields therewith, peripheral delineation, blind spots and the like.

As another non-limiting example, there can be cited the genito-urinary tract. Not only can anatomical abnormalities discovered in diagnosis be charted and recorded, but also such occurrences as kidney stones can be precisely located for the record, and the size and progress thereof through the tract be recorded.

Similar applications are for the brain, the digestive tract, the lungs and chest, heart, face and the limbs and extremities. Depending on the breadth and extent of his practice, the physician and surgeon can avail himself of one or more of these reproducing devices as needed, such as in the form of a rubber stamp, which may be hand-inked or self-inked, each at a nominal cost, yet saving much valuable time in the necessary record keeping, while contributing great accuracy and precision in enabling charting the results of diagnosis and other pertinent information, with concurrent benefits to the patient and the physician.

Although the invention has been described with respect to specific details of certain embodiments thereof, it is not intended that such details act as limitations upon the scope of the invention except insofar as set forth in the accompanying claims.

I claim:

1. A method of recording in a patient's record, medical examination findings or surgical information involving anatomical considerations, which comprises reproducing in said record in the desired appropriate space thereof, an anatomical chart, diagram or graphic representation of the body area involved, having superimposed thereon a series of concentric circles and equidistant radial line extensions from a center representing an anatomical point of reference of said body area, by means of a reusable ink print transfer reproducing device and thereafter completing the record by making appropriate markings on said imprint and adjacent thereto, to record the location, size and kind of any abnormality or anatomical consideration, so as to depict accurately the aforesaid medical and surgical findings.

2. The method of claim 1 in which the body area in the record print is a woman's breast and the anatomical center point of reference is the nipple and areola thereof.

3. The method of claim 2 in which the distance between the concentric circles represents the breadth of a physician's finger and the radial lines represent the twelve position hours on a timepiece.

4. The method of claim 1 in which the body area in the record print is that of the eye.

5. The method of claim 1 in which the body area in the record print is that of a kidney.

6. The method of claim 1 in which the ink transfer reproducing device is in the form of a self inking or hand inking rubber stamp type.

7. The method of claim 1 in which the print is correctly aligned in the record space by means of a guide on the ink print transfer device, said guide comprising spaced semi-circles and spaced angular lines cutting across said semi-circles with one vertical line bisecting said semi-circles, said guide being located on a vertical side of the ink print transfer device.

* * * * *